United States Patent [19]

Trick

[11] Patent Number: 4,917,110
[45] Date of Patent: Apr. 17, 1990

[54] PENILE PROSTHESIS

[75] Inventor: Robert E. Trick, Racine, Wis.

[73] Assignee: Medical Engineering Corporation, Racine, Wis.

[21] Appl. No.: 249,728

[22] Filed: Sep. 27, 1988

Related U.S. Application Data

[63] Continuation-in-part of Ser. No. 145,629, Jan. 19, 1988, which is a continuation-in-part of Ser. No. 887,069, Jul. 17, 1986, Pat. No. 4,726,360.

[51] Int. Cl.$^4$ .................................................. A61F 2/26
[52] U.S. Cl. ......................................................... 128/79
[58] Field of Search .................. 128/79, 899; 251/342; 600/29, 30, 31

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,204,530 | 5/1980 | Finney | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,424,807 | 1/1984 | Evans, Sr. | 128/79 |
| 4,449,520 | 5/1984 | Palomar et al. | 128/79 |
| 4,550,719 | 11/1985 | Finney et al. | 128/79 |
| 4,550,720 | 11/1985 | Trick | 128/79 |
| 4,572,168 | 2/1986 | Fischell | 128/79 |
| 4,574,792 | 3/1986 | Trick | 128/79 |
| 4,590,927 | 5/1986 | Porter et al. | 128/79 |
| 4,594,997 | 6/1986 | Hakky | 128/79 |
| 4,596,242 | 6/1986 | Fischell | 128/79 |
| 4,622,958 | 11/1986 | Finney | 128/79 |
| 4,682,589 | 7/1987 | Finney | 128/79 |
| 4,718,410 | 1/1988 | Hakky | 128/79 |
| 4,726,360 | 2/1988 | Trick et al. | 128/79 |

Primary Examiner—Cary E. Stone
Attorney, Agent, or Firm—Quarles & Brady

[57] ABSTRACT

An implantable prosthesis for correcting erectile impotence includes at least one penile implant with a pressure chamber, an accumulator charged with fluid, tubing connecting the accumulator to the pressure chamber of the implant, a valve which is normally closed and a lever which can be moved to open the valve so that pressurizing fluid will flow from the accumulator into the pressure chamber.

8 Claims, 2 Drawing Sheets

U.S. Patent    Apr. 17, 1990    Sheet 1 of 2    4,917,110
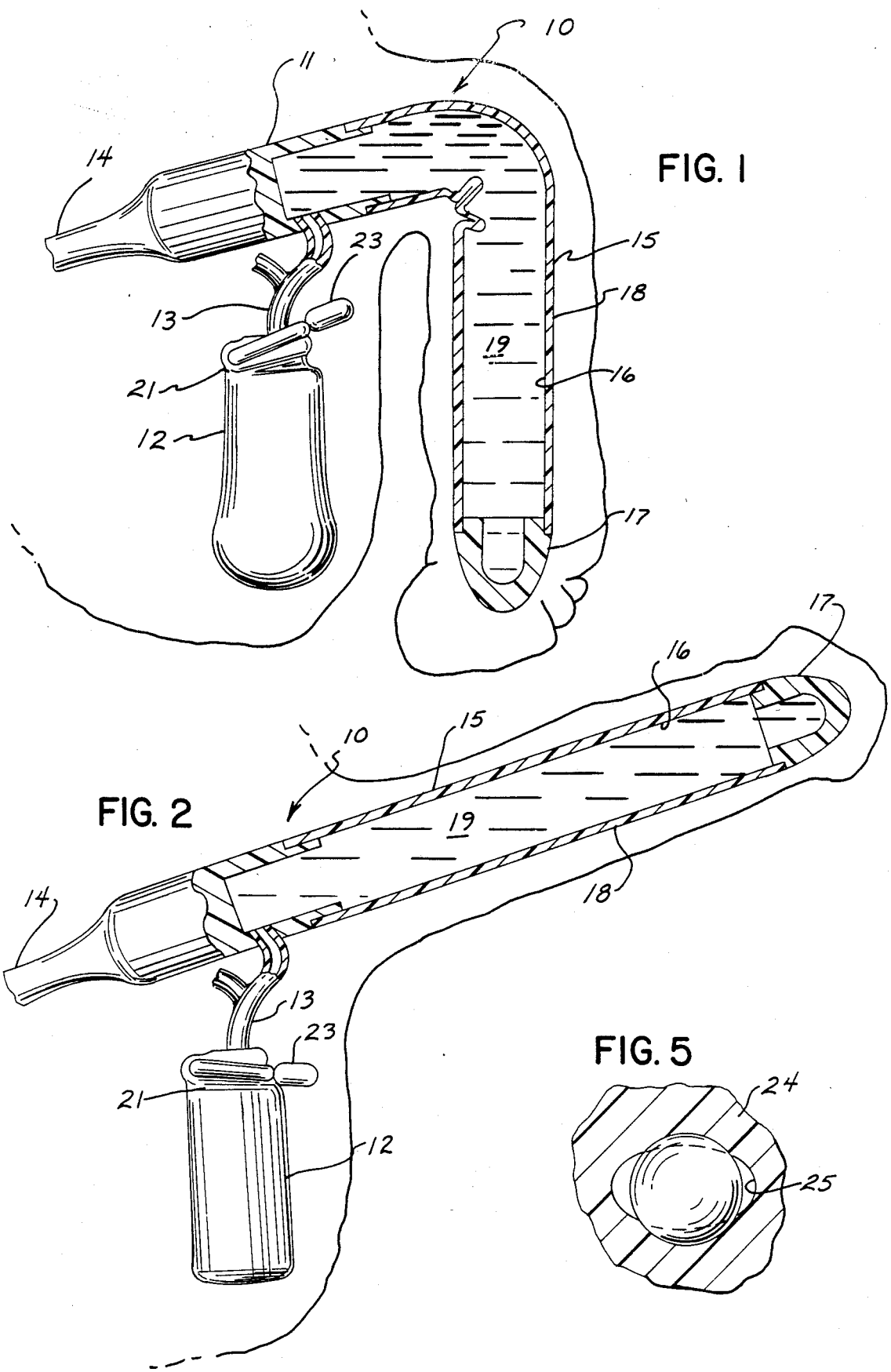

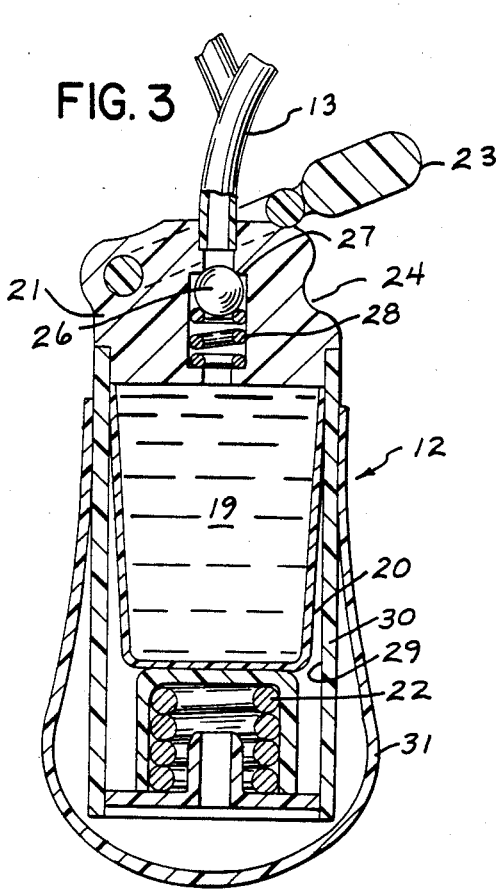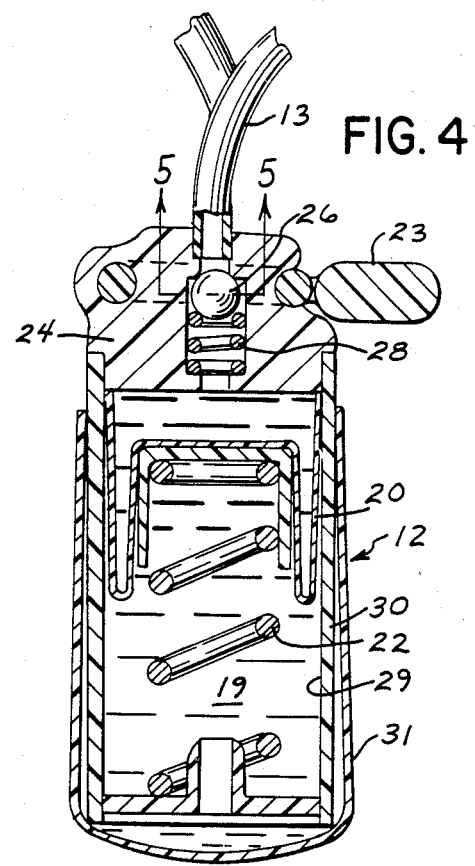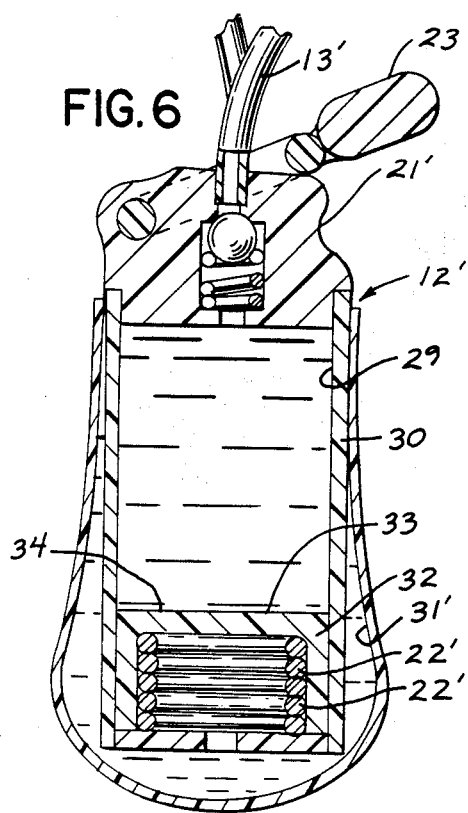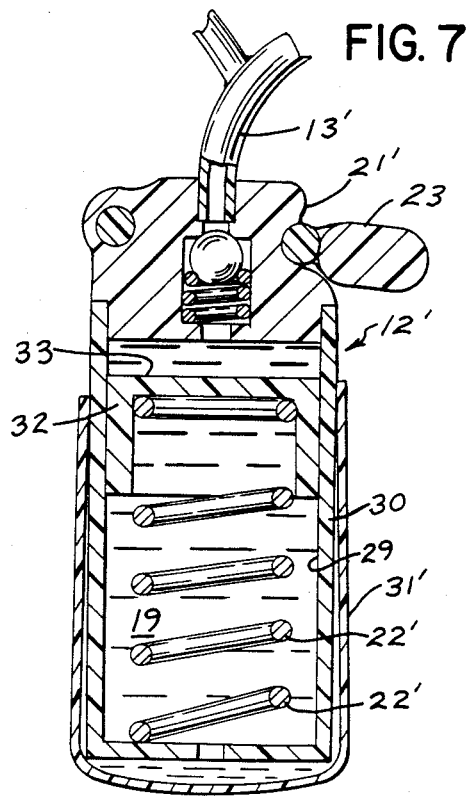

PENILE PROSTHESIS

RELATED CASES

This is a continuation-in-part of my pending application Ser. No. 145,629 filed Jan. 19, 1988, which is a continuation-in-part of my application Ser. No. 887,069, pending, filed July 17, 1986, now U.S. Pat. No. 4,726,360, issued Feb. 23, 1988.

FIELD OF THE INVENTION

The present invention relates to a penile prosthesis. More particularly, it relates to an inflatable penile prosthesis which is adapted to be implanted in man for treatment of erectile impotence.

BACKGROUND OF THE INVENTION

There are instances of erectile impotence in which the patient does not respond to more conventional therapy and the surgical implanting of a penile prosthesis may be the only practical means of remedying the impotency.

Several types of penile prostheses have been employed in the past. One type of penile prosthesis is a pair of rods of suitable stiffness which are surgically implanted into the corpus cavernosum of the penis. One disadvantage of some of the rod-type implants is the permanent stiffness of the rod which can be a source of physical pain and/or embarrassment to the patient. The prostheses disclosed in U.S. Pat. No. 3,893,476 and U.S. Pat. No. 4,066,073 are representatives of the rod type prostheses.

Another type of penile prosthesis which is available is the inflatable prosthesis of U.S. Pat. No. 3,954,102. The patented prosthesis includes two fairly long inflatable and distensible tubes that are surgically implanted in the corpus cavernosum of the penis. Each of the two tubes is connected by tubing to a manually operable pressure bulb for inflating fluid, which is implanted in the scrotal sac, and a reservoir which is placed in the abdominal cavity. The operation required to implant the prosthesis is relatively complex and lengthy.

Recently, penile prostheses have been patented and made commercially available which are essentially cylinders which contain a hydraulic system comprising a pressure chamber, a reservoir and a manually operable pump for transferring fluid from the reservoir to the pressure chamber. The operation for placing the cylinders in the corpora cavernosa is relatively simple and quick. Representative of such implants are those of U.S. Pat. Nos. 4,353,360, 4,267,829 and 4,383,525.

Still more recently, a penile prosthesis has been made commercially available that comprises two implants containing pressure chambers that are implanted in the corpora, a manually operable pump that is implanted in the scrotal sac and connecting tubing. This type of prosthesis is relatively less expensive than the self-contained cylinders. The surgical procedure for implanting this type of prosthesis is relatively simple and does not require abdominal surgery. Representative of this prosthesis is the prosthesis of U.S. Pat. No. 4,726,360 and others.

Although the previously patented prostheses are useful and valuable devices, it would be desirable to have an improved penile prosthesis which does not require manual pumping to achieve an erection. A number of designs for such prosthesis have been proposed and patented but none have become commercially available.

SUMMARY OF THE INVENTION

It is the general object of the present invention to disclose an improved penile prosthesis that does not require manual pumping to achieve an erection.

The penile prosthesis of the present invention basically comprises a pair of penile implants each having a pressure chamber which is connected by tubing to a charged accumulator which is actuated to pressurize the pressure chambers by simply moving a lever.

Each of the implants of the prosthesis of the present invention is an elongated cylindrical member which is to be implanted into a corpus cavernosum of the penis. The pressure chambers of the implants are connected by the tubing to the charged accumulator which is implanted in the scrotal sac.

In a preferred embodiment, the proximal portion of implant of the present invention includes an anchoring stem which is relatively stiff so that it can be implanted into the root end of the corpus cavernosum to support the implant. The remainder of the implant is of a less stiff and softer material which reduces the risk of tissue irritation. When not pressurized the cylindrical member is flexible and permits the pendulus penis to assume a normal flaccid position. The tip at the distal end of the implant is conical to fit the end of the corpus cavernosum, and to enhance the physiological compatibility of the implant.

The charged accumulator of the preferred embodiment includes a bladder for pressurizing fluid which is normally filled with the fluid and maintained in that state by a valve which when closed prevents fluid from leaving the bladder. The accumulator is activated to pressurize the pressure chamber by moving a lever to open the valve. When the valve is open a compressed spring expands and forces the fluid from the bladder to the pressure chambers causing them to become hard and rigid.

In another embodiment of the invention, the accumulator has a fluid chamber of which the bottom is the head of a spring activated piston. In this embodiment, the chamber is normally full of fluid and of maximum volume when the valve is closed and of reduced volume when the valve is open.

The prosthesis of the present invention provides advantages over prior art prostheses that rely upon relief valves for protection against over pressure because the accumulator does not leak down and result in a loss of fluid. In addition, it has advantages over the prostheses that have no protection against overpressure. When an overpressure occurs in an accumulator equipped prosthesis the increased pressure is absorbed by fluid returning to the accumulator; when the overpressure is relieved the fluid returns to the pressure chamber.

BRIEF DESCRIPTION OF THE DRAWINGS

In the drawings:

FIG. 1 is a side view, partly in section, of a preferred embodiment of the prosthesis of the present invention. The implant is shown in a non-pressurized state with the accumulator charged;

FIG. 2 is a side view similar to FIG. 1, except that the implant is pressurized;

FIG. 3 is an enlarged sectional view of the accumulator of FIG. 1;

FIG. 4 is a view like FIG. 3 of the accumulator of FIG. 2;

FIG. 5 is a view taken along lines 5—5 of FIG. 4 showing the valve body deformed to create flow passages;

FIG. 6 is a view like FIG. 3 of another embodiment of the accumulator; and

FIG. 7 is a view like FIG. 4 of the accumulator of FIG. 6.

PREFERRED EMBODIMENT OF THE INVENTION

The preferred penile prosthesis 10, which is shown in FIGS. 1 and 2, comprises a pair of identical cylindrical penile implants 11 of which only one is shown, an accumulator 12 and connecting tubing 13.

As seen in FIGS. 1 and 2 of the drawings, the generally cylindrical member 11 has a short proximal stem 14 and a longer distal portion 15, which includes a pressure chamber 16 and a conical distal tip 17. The stem 14 which is of a relatively stiff material is implanted in the root end of a corpus cavernosum. The remaining or distal portion 15 is implanted in the portion of the corpus in the pendulous penis. Each of the two cylindrical members 11 is positioned in a separate corpus cavernosum of the penis and are connected by the tubing 13 to the accumulator 12 which is implanted in the scrotal sac.

The wall 18 of the pressure chamber 16 of the implant 11 may be of either a distensible or non-distensible material. A non-distensible material is preferred so that the chamber 16 can be pressurized with a relatively small amount of fluid to become hard and rigid. A suitable, non-distensible material is reinforced silicone rubber or polyurethane which either does not stretch or stretches only a given amount. The necessary fluid tight seals between the wall 18, the stem 14 and the tip 17 may be made with a silicone adhesive or by other suitable means.

When the prosthesis 10 is in a non-pressurized state as seen in FIG. 1, the chamber 16 is partially filled with a non-compressible hydraulic fluid 19 which is biocompatible, such as saline or a free flowing silicone gel. In the non-pressurized state, the distal portion 15, including chamber 16, flexes and permits the penis to assume a substantially normal, flaccid position.

When the prosthesis 10 is as seen in FIG. 1, the accumulator 12 is in the state seen in FIG. 3. As seen there, the accumulator 12 includes a bladder 20 which is full of fluid 19; the fluid 19 is prevented from flowing from the bladder 20 to the chamber 16 via the tubing 13 by a valve 21 which is closed. As seen in FIG. 3, when the valve 21 is closed and the bladder 20 is full of fluid 19, a spring 22 positioned in the accumulator 12 below the bottom of bladder 20 is compressed.

In FIG. 2, it can be seen that the distal portion 15 of the implant 11 is rigid as the result of the pressure chamber 16 being completely filled with fluid 19 under pressure.

The pressurized state seen in FIG. 2 is achieved by discharging the normally charged accumulator 12 by opening the valve 21 by moving a lever 23 from the position seen in FIG. 3 to the position seen in FIG. 4. When the lever 23 is moved to the position seen in FIG. 4, the valve 21 is opened by deforming the valve housing 24 to create flow passages 25 seen only in FIG. 5, around a ball 26 which is normally kept on a seat 27 by a precalibrated spring 28. When the lever 23 is as seen in FIG. 4 the fluid 19 from the bladder 20 is forced through the flow passages 25 in the valve 21 into the tubing 13 and into the chamber 16 by the expansion of the spring 22 which collapses the bladder 20.

The bladder 20 is preferably of a highly flexible, high strength membrane, such as nylon, which can be repeatedly collapsed and expanded without showing signs of fatigue. As seen in FIGS. 3 and 4 it is housed in the bore 29 of a relatively rigid cylindrical member 30 which is in turn enclosed within a fluidtight protective outer cover 31.

When it is desired to cause the prosthesis 10 to assume the normal, non-pressurized position seen in FIG. 1, the pressure chamber 16 is partially emptied and depressurized by moving the lever 23 to the position seen in FIG. 3 where it no longer deforms the housing 24 and either bending or squeezing the distal portion 15 of the implant 11 to increase the fluid pressure in the chamber 16 and tubing 13 enough to move the ball 26 back off its seat 27 and to compress the spring 28. As the fluid pressure in the bladder 20 increases, the spring 22 is once again compressed. When sufficient fluid 19 has been transferred back to the accumulator 12, the distal portion 15 will be soft and the prosthesis will assume the flaccid state seen in FIG. 1.

When the implant is pressurized as seen in FIG. 2, the valve 21 is open so that excessive pressures are not generated in the pressure chamber 16 during intercourse. Any accidental bending of the implant or other event that might otherwise cause excessive pressures merely results in fluid being returned to the accumulator 12 and the bladder 20. As the bladder 20 increases in size a small amount of fluid is displaced into the protective cover 31. Thus, accidental damage to the prosthesis from an overpressure is prevented.

In FIGS. 6 and 7, an embodiment of the accumulator 12' is seen that does not include a bladder. In place of the bladder 20 of the first embodiment, the accumulator 12' includes a spring driven piston 32 which has a head 33 which fits within the bore 29 of the cylindrical member 30. The head 33 of the piston 32 forms a fluid tight seal with the wall of the bore 29 and as seen in FIG. 6 forms the bottom of a chamber 34.

As seen in FIG. 6, when the accumulator 12' is charged with fluid and the valve 21' is closed the spring 22' is compressed. However, when the valve 21' is opened, the compressed spring 22' expands to drive the fluid which is in the chamber 34 in front of the piston head 33, through the tubing 13' forceably under pressure, into the pressure chamber 16.

The accumulator 12' of FIGS. 6 and 7 can be depressurized and reacts to overpressure in the same manner as described for accumulator 12.

As seen in FIGS. 3 and 6, the fluidtight, outer protective covers 31, 31' which are elastic contain fluid 19 which freely flows into the cylindrical member 30 when the spring 22, 22' expands as seen in FIGS. 4 and 7, respectively.

All the components of the described implants are preferably made of biocompatible materials having the necessary properties to function as intended.

The term "partially filled" as used herein to describe the fluid content of a chamber in the penile implant means that a chamber contains about 60% or more of its capacity of a non-compressible fluid such as saline or a free flowing gel. The actual content of fluid can vary; however, the implant when "partially filled" should be still sufficiently flexible so that the penis can assume a normal flaccid position.

The term "non-distensible" as used herein is intended to cover materials or components which do not distend or distend to only a limited extent which still permits the device to function as intended.

All the parts and components of the prosthesis are preferably made of materials which are non-reactive, non-toxic and well tolerated by the adjacent organic tissues. Silicone rubber is preferred where the prosthesis makes contact with tissue because it is quite resistant to wear and remains functional for a long period of time. However, other suitable materials possessing desirable properties may also be employed.

The preferred method of implantation of the prosthesis is through incisions made in the penis and the scrotal sac. After appropriate incisions, each corpus cavernosum is dilated distally and proximally to accept the implants. The appropriate anatomical measurements are made to insure that the proximal end of the implant or implants will be positioned in the proximal crus. An appropriately sized implant is then inserted into the corpus cavernosum of the penis. The distal tip is positioned in the glans end of the corpus cavernosum. The stem at the proximal end of the implant is anchored in the root end of the corpus cavernosum. The tubing is threaded through the patient's body to the accumulator which is placed in the scrotal sac. The incisions are then closed.

It will be understood that the foregoing description has been for purposes of illustration, and a number of changes may be made without departing from the spirit and scope of the invention. Therefore, the invention is not to be limited except by the claims which follow.

I claim:

1. In an implantable prosthesis for correcting erectile impotence which includes at least one flexible penile implant with a pressure chamber for implanting in a patient's penis, transfer means for transferring fluid to the pressure chamber for implanting in the patient's scrotal sac and tubing connecting said pressure chamber to said transfer means, the improvement which comprises said transfer means being a charged accumulator and means for discharging said accumulator, said means for discharging being a manually operable lever and a valve which can be opened by moving said lever.

2. An implantable prosthesis of claim 1 in which said accumulator includes a fluidtight protective outer cover.

3. An implantable prosthesis of claim 1 in which the valve includes a deformable housing which is deformed to operate flow passages when the lever is moved.

4. An implantable prosthesis of claim 1 in which the pressure chamber is non-distensible.

5. A penile erectile system includes:
   (a) at least one elongated cylindrical penile implant for implanting in the corpus cavernosum of a penis, said implant having a pressure chamber;
   (b) an accumulator charged with fluid for pressurizing the pressure chamber;
   (c) tubing connecting the pressure chamber of the implant and the accumulator;
   (d) valve means between the pressure chamber and the accumulator, said valve means being normally closed; and
   (e) a manually operable movable lever for opening the valve means and discharging the accumulator.

6. The system of claim 5 in which the valve means has a deformable housing and it is manually opened by moving the lever to deform the housing and to create flow passages.

7. A penile erectile system includes:
   (a) at least one elongated cylindrical penile implant for implanating in the corpus cavernosum of a penis, said implant having a pressure chamber;
   (b) an accumulator charged with fluid for pressurizing the pressure chamber;
   (c) tubing connecting the pressure chamber of the implant and the accumulator;
   (d) valve means between the pressure chamber and the accumulator, said valve means being normally closed;
   (e) a manually operable movable lever for opening the valve means and discharging the accumulator; and
   (f) means in the accumulator for a forcing fluid from the accumulator to the pressure chamber when the valve means is opened by moving the lever.

8. The system of claim 7 in which the means for forcing fluid is a compressed spring.

* * * * *